United States Patent [19]

Cotrel

[11] Patent Number: 5,154,719
[45] Date of Patent: Oct. 13, 1992

[54] IMPLANT FOR A DEVICE FOR OSTEOSYNTHESIS, IN PARTICULAR OF THE SPINE

[75] Inventor: Yves Cotrel, Paris, France

[73] Assignee: Societe de Fabrication de Materiel Orthopedique - Sofamor, Paris, France

[21] Appl. No.: 656,823

[22] Filed: Feb. 19, 1991

[30] Foreign Application Priority Data

Feb. 19, 1990 [FR] France ............... 90 01972

[51] Int. Cl.⁵ .............................. A61F 2/44
[52] U.S. Cl. ........................ 606/73; 606/72
[58] Field of Search ............ 606/72, 73, 53, 60, 606/61, 74

[56] References Cited

U.S. PATENT DOCUMENTS

| 4,013,071 | 3/1977  | Rosenberg    | 606/73   |
|-----------|---------|--------------|----------|
| 4,041,939 | 8/1977  | Hall         | 606/73   |
| 4,484,570 | 11/1984 | Sutter et al.| 606/72   |
| 4,524,765 | 6/1985  | De Zbikowski | 606/73   |
| 5,013,313 | 5/1991  | Surer        | 606/72 X |

FOREIGN PATENT DOCUMENTS

| 0348272    | 12/1989 | European Pat. Off. . |        |
|------------|---------|----------------------|--------|
| 2559378    | 8/1985  | France .             |        |
| 2624720    | 6/1989  | France .             |        |
| 2642643    | 8/1990  | France .             |        |
| WO90/09156 | 8/1990  | PCT Int'l Appl. .    |        |
| 2154296    | 9/1985  | United Kingdom       | 606/73 |
| 2173104A   | 10/1986 | United Kingdom .     |        |

Primary Examiner—Robert A. Hafer
Assistant Examiner—Sam Rimell
Attorney, Agent, or Firm—Wenderoth, Lind & Ponack

[57] ABSTRACT

An implant comprises a part intended for osseous anchoring and a body for fixation on a rod. The body has a channel opening out at a rear part of the body, delimiting two lateral branches and open on each side of the body so as to be able to receive the rod. The implant also comprises a threaded plug adapted so as to be able to be screwed in tappings formed on the inside walls of the two lateral branches in order to lock the rod in translation and in rotation. The implant includes a small plate for connection between the plug and the rod, which small plate is provided with a mechanism for fixing it to the branches of the body.

8 Claims, 2 Drawing Sheets

IMPLANT FOR A DEVICE FOR OSTEOSYNTHESIS, IN PARTICULAR OF THE SPINE

BACKGROUND OF THE INVENTION

The present invention relates to an implant for a device for osteosynthesis, in particular of the spine, of the type comprising a part intended for osseous anchoring and a body for fixation on a rod, in which the body presents a channel opening out at a rear part of the body, delimiting two lateral branches and open on each side of the body so as to be able to receive the rod. This implant also comprises a threaded plug adapted so as to be able to be screwed in a tapping formed in the inside walls of the two lateral branches in order to lock the rod in translation and in rotation.

Such an implant is described in French Patent Application 88/08,538 (Publication No. 2,633,177) filed on Jun. 24th, 1988 by the Applicant. This device, which permits fixation of a knurled rod to a vertebra, has certain disadvantages:

on the one hand, there is some difficulty in moving the rod after positioning of the threaded plug for fixation, and on the other hand, the branches of the U-shaped body may undergo a certain spacing apart during tightening of the plug on the rod.

SUMMARY OF THE INVENTION

The object of the invention is therefore to overcome the above disadvantages.

According to the invention, the implant comprises a small plate for connection between the plug and the rod, which a small plate is provided with means for fixing it to the branches of the body.

Thus, upon tightening of the plug, the small plate comes to bear on the rod and immobilizes it completely in the body of the implant, and at the same time the means for fixing of the small plate to the branches of the body counter any spacing apart of the branches.

According to one embodiment of the invention, the means for fixing of the small plate to the branches is made up of a ring surrounding the branches and integral with the ends of the small plate, which extends from one end to the other of the channel of the body, it being possible for the branches of the body to be introduced into passages between the ring and the edges of the small plate.

The small plate and the ring can be made unitary, i.e. out of one piece, the ring surrounding the two branches and countering their being spaced apart upon screwing in the threaded plug.

BRIEF DESCRIPTION OF THE DRAWINGS

The invention will now be described with reference to the attached drawings which illustrate one embodiment thereof by way of a non-limiting example.

DETAILED DESCRIPTION OF THE PREFERRED EMBODIMENT

Figure 1:
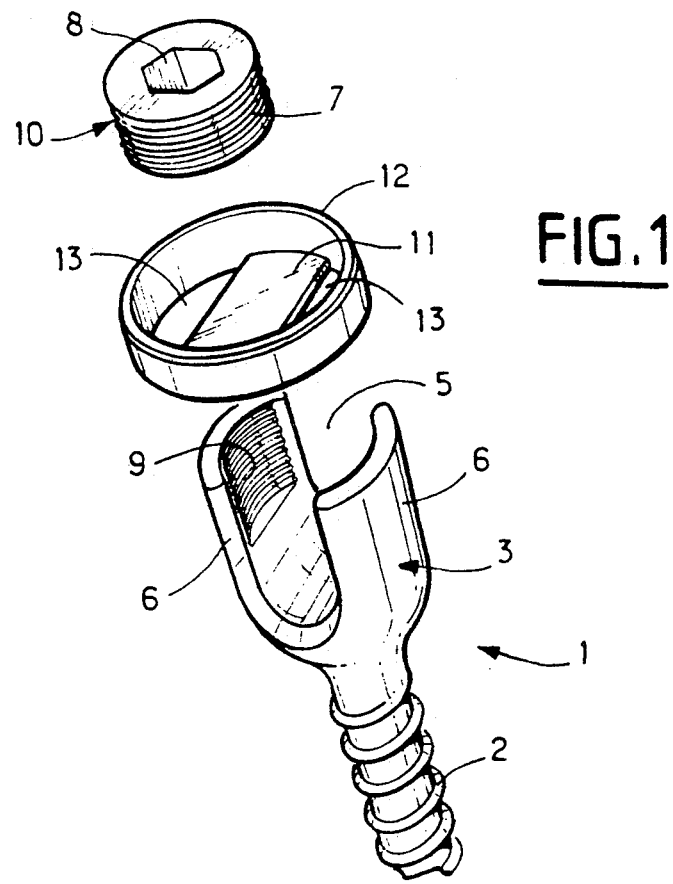
FIG. 1 is an exploded perspective view of an embodiment of the implant according to the invention.
Figure 2:
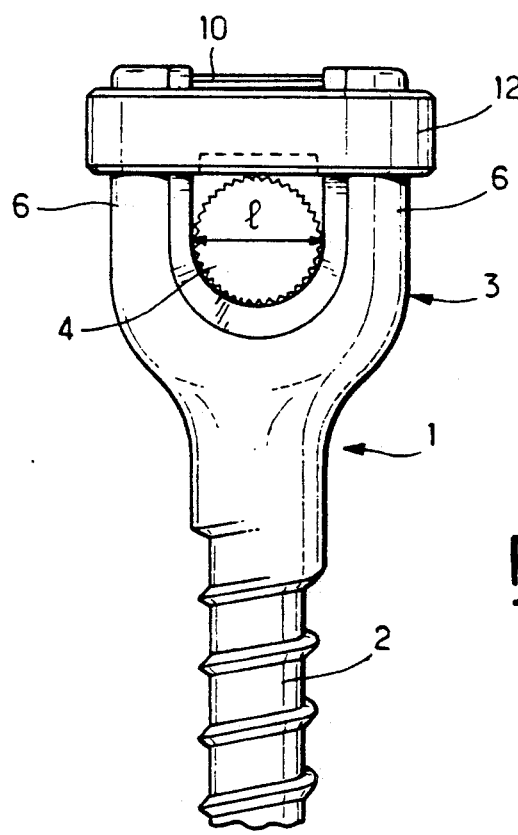
FIG. 2 is an elevation view of the implant in FIG. 1, equipped with a corresponding rod locked in a channel of body by panel and plug.
Figure 3:
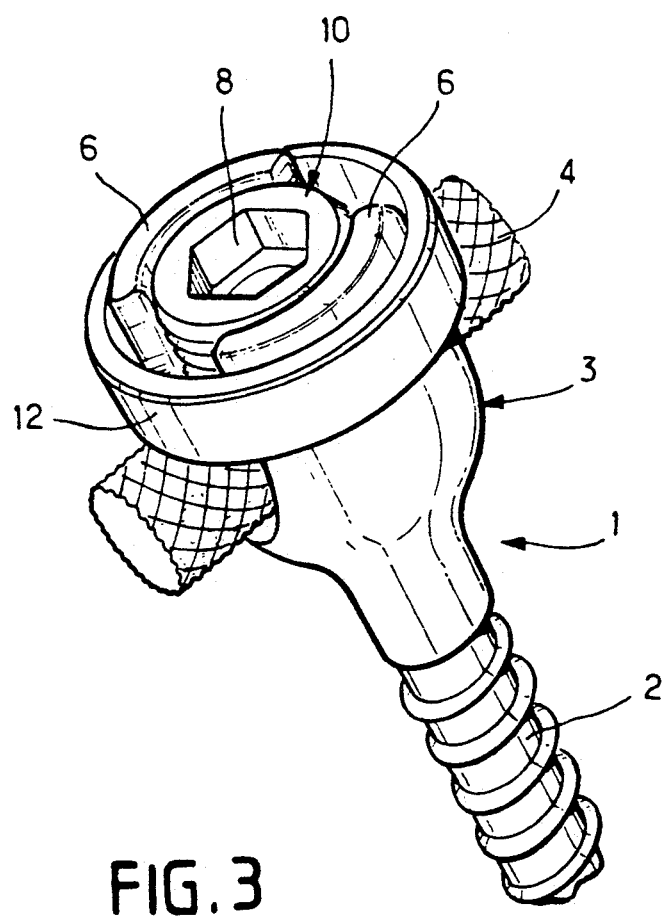
FIG. 3 is a perspective view of the implant in FIG. 2 and of a section of the corresponding rod.

The implant 1 shown in the drawings is intended for a device for osteosynthesis (not shown), in particular for the spine. It comprises a part 2 intended for osseous anchoring and here consisting of a threaded rod, which can be replaced by a hook as in the implant described in French Patent Application 2,633,177, mentioned above.

The implant also comprises a body 3 for fixation on a rough-surfaced rod 4, for example a knurled or diamond-pointed rod. The body 3 presents a channel 5 opening out at a rear part of the body, delimiting two lateral branches 6 and open on each side of the body so as to be able to receive the rod 4. The body 3 thus has a U-shaped cross-section in a plane transverse to the channel 5.

The implant is also equipped with a plug 10 provided with a thread 7 and in which there is machined a recess 8 suitably profiled for receiving a corresponding tool for screwing the plug 10 in tappings 9 on the inside walls of the branches 6. The implant 1 comprises a small plate 11 for connection between the plug 10 and the rod 4, which small plate extends from one end to the other of the channel 5 and whose width is slightly less than the width 1 of the inlet of the channel 5. The ends of the small plate 11 are integral with a ring 12, which is preferably cylindrical and which surrounds the two branches 6 when it is positioned on the body 3 by inserting the branches 6 in the passages 13 reserved between the inside wall of the ring 12 and the longitudinal edges of the small plate 11.

The small plate 11 and the ring 12 can be attached to one another or preferably form one piece. The small plate 11 connects two diametrically opposed portions of the edge of the cylindrical ring 12 directed towards the base of the channel 5.

The positioning of the various elements constituting this implant and the locking of the rod 4 are carried out in a very simple manner. The rod 4 is at first introduced into the channel 5, then the ring 12 is passed around the ends of the branches 6 until the small plate or panel 11 comes to bear on the rod 4, the branches 6 fitting between the ring 12 and the longitudinal edges of the small plate 11. Finally, the plug 10 is introduced between the ends of the branches 6, and it is screwed in the tappings 9 until its plane surface opposite the cavity 8 locks on the small plate 11. The latter is thus applied firmly on the roughened surface of the rod 4, which is locked in translation and in rotation.

With such a device, it is no longer necessary to arrange a catch on the surface of the plug 10 oriented towards the rod 4, in contrast to what is intended in French Patent 2,633,177. Moreover, it is possible to move the rod slightly in order for it to find its definitive position after putting the small plate 11 and the ring 12 into place and before tightening the plug 10. Finally, the height of the ring 12 can vary.

I claim:

1. An implant for an osteosynthesis device, comprising:

an implant body, said body having two lateral branches defining a channel for receiving a rod therein;

an anchor connected to said implant body of osseous anchoring of said implant body;

threads formed on the inside walls of said lateral branches;

a threaded plug threaded in said threads of said lateral branches for fixing a rod to be received by said channel, and a plate below said plug, said plate, having a means for fixing said plate to said lateral branches of said implant body.

2. The implant of claim 1, wherein said means for fixing said plate to said lateral branches of said implant body comprises a ring surrounding said lateral branches of said implant body comprises a ring surrounding said lateral branches and integral with opposite ends of said plate, said plate extending along said channel defined by said lateral branches from one end of said channel to the other, wherein said ring and the edges of said plate together define passages through which said lateral branches are received.

3. The implant of claim 2, wherein said plug has a plane surface bearing on said plate.

4. An implant in an osteosynthesis device, said implant comprising:

an implant body having two lateral branches defining a channel, each said lateral branch having a threaded inner surface;

an anchor connected to said implant body for osseous anchoring of said implant body;

a threaded plug to be threaded in said threads of said lateral branches of said implant body; and engaging means for engaging a rod to be received in said channel by being pressed by said threaded plug, said engaging means comprising a small plate and a means for attaching said small plate to said lateral branches of said implant body.

5. The implant of claim 4, wherein said means for attaching also is a means for preventing said lateral branches of said implant body from being moved apart from each other by said threaded plug.

6. the implant of claim 5, wherein said means for attaching is a ring surrounding said lateral branches and connected to said small plate.

7. The implant of claim 6, wherein said small plate extends along said channel, and has opposite ends integral with said ring.

8. The implant of claim 7, wherein said small plate and said ring are one-piece.

* * * * *